US00PP07790P

United States Patent [19]

VandenBerg

[11] Patent Number: Plant 7,790

[45] Date of Patent: Feb. 11, 1992

[54] CHRYSANTHEMUM PLANT NAMED CREAM FROLIC

[75] Inventor: Cornelis P. VandenBerg, Salinas, Calif.

[73] Assignee: Yoder Brothers, Inc., Barberton, Ohio

[21] Appl. No.: 599,348

[22] Filed: Oct. 18, 1990

[51] Int. Cl.[5] ..... A01H 5/00

[52] U.S. Cl. ..... Plt./78

[58] Field of Search ..... Plt./77, 78

[56] References Cited

U.S. PATENT DOCUMENTS

P.P. 6,620 2/1989 Mack et al. ..... Plt. 77

*Primary Examiner*—James R. Feyrer

*Attorney, Agent, or Firm*—Foley & Lardner

[57] ABSTRACT

A Chrysanthemum plant named Cream Frolic particularly characterized by its flat capitulum form; decorative capitulum type; cream ray floret color with light yellow center of the flower; diameter across face of capitulum of 52 to 54 mm. when fully opened; spreading and prolific branching pattern, with 6 to 9 breaks after pinch when grown outside under natural daylength in fall flowerings, and 3 to 6 breaks after pinch when grown in 10 cm. pots for spring flowerings; natural season flowering date of August 28 when planting rooted cuttings June 23 in Salinas, Calif., and September 30 when planting rooted cuttings June 15 to June 18 in Hightstown, N.J.; flowering response of 49 to 59 days after rooting in no light/no shade programs in spring; plant height of 30 to 33 cm. when grown in fall under natural daylength with no growth regulators, and 20 to 25 cm. when grown in 10 cm. pots in spring with 1 to 2 applications of 2500 ppm B-9 SP; and durable, uniform performance.

1 Drawing Sheet

The present invention comprises a new and distinct cultivar of Chrysanthemum, botanically known as *Dendranthema grandiflora,* and referred to by the cultivar name Cream Frolic.

Cream Frolic, identified as 83-MO5C15, is a product of a mutation induction program. The new cultivar was discovered and selected by Cornelis P. VandenBerg on July 20, 1987 in a controlled environment in Salinas, Calif., as one flowering plant within a flowering block established as rooted cuttings from stock plants which had been exposed as unrooted cuttings to an x-ray source of 1500 rads. The irradiated parent cultivar was Frolic, a white flat decorative spray pot mum and garden mum, disclosed in U.S. Plant Pat. No. 6,620.

The irradiation program resulting in Cream Frolic had as its primary objective the expansion of color ranges of Frolic, which is white in ray floret color. The program comprised irradiating cuttings of the parent cultivar Frolic at irradiation levels of 1500, 1750 and 2000 rads. A total of 820 irradiated plants were planted April 20, May 11 and May 25, 1987. Of These, 14 initial selections were made, which selections were then revegetated and reflowered. Of the entire group, only Cream Frolic was selected (on June 20, 1987) for commercial introduction. Although color expansion was the objective of the program, the induced mutation Cream Frolic quite unexpectedly distinguishes from the parent cultivar Frolic in other respects as well, as will be noted.

The first act of asexual reproduction of Cream Frolic was accomplished when vegetative cuttings were taken from the initial selection in September 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Cream Frolic are firmly fixed and are retained through successive generations of asexual reproduction.

Cream Frolic has not been observed under all possible environmental conditions. The phenotype may vary significantly with variations in environment such as temperature, light intensity and daylength.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Cream Frolic, which, in combination, distinguish this Chrysanthemum as a new and distinct cultivar:

1. Flat capitulum form.
2. Decorative capitulum type.
3. Cream ray floret color with light yellow center of capitulum.
4. Diameter across face of capitulum of 52 to 54 mm. when fully opened.
5. Branching pattern is spreading and prolific, with 6 to 9 breaks after pinch when grown outside under natural daylength in fall flowerings, and 3 to 6 breaks after pinch when grown in 10 cm. pots for spring flowerings.
6. Natural season flower date of August 28 when planting rooted cuttings on June 23 in Salinas, Calif., and of September 30 when planting rooted cuttings June 15 in Hightstown, N.J.
7. Flowering response of 49 to 59 days after rooting in no light/no shade programs in spring.
8. Plant height of 30 to 33 cm. when grown in fall under natural daylength with no growth regulators, and of 20 to 25 cm. when grown in 10 cm. pots in spring with 1 to 2 applications of 2500 ppm B-9 SP.

9. Durable, uniform performance.

The accompanying photographic drawing is a color photograph of Cream Frolic grown as a pinched pot mum with four cuttings in a 15 cm. pot, with the colors being as nearly true as possible with illustrations of this type.

Of the commercial cultivars known to the inventor, the most similar in comparison to Cream Frolic is the parent cultivar Frolic. Most traits of Cream Frolic are similar to those of Frolic, except ray floret color, vigor and response. The flower color of Cream Frolic is a two-tone cream/light yellow, while the flower color of Frolic is white. In several of our flowering trails Cream Frolic had a greater vigor by 2.5 to 5 cm. than Frolic, and a slightly faster flowering response by one to two days when compared with Frolic.

In the following description color references are made to The Royal Horticultural Society Colour Chart. The color values were determined on plant material grown as a pinched spray pot mum in Salinas, Calif. on May 3, 1990.

Classification:

*Botanical.*—*Dendranthema grandiflora* cv Cream Frolic.

*Commercial.*—Flat decorative spray pot mum and garden mum.

INFLORESCENCE

A. Capitulum:

*Form.*—Flat.

*Type.*—Decorative.

*Diameter across face.*—52 to 54 mm. when fully opened.

B. Corolla of ray florets:

*Color (general tonality from a distance of three meters).*—Cream with a light yellow center.

*Color (upper surface).*—Outer ray florets, 9D; center of flower, 8B to 8C.

*Color (under surface).*—9D.

*Center of opening buds.*—Slightly overlaid with 144B.

*Shape.*—Spooned. Longitudinally straight, cross section concave.

C. Corolla of disc florets:

*Color (mature).*—9B.

*Color (immature).*—144A.

D. Reproductive organs:

*Androecium.*—Present on disc florets only; moderate pollen.

*Gynoecium.*—Present on both ray and disc florets.

PLANT

A. General appearance:

*Height.*—30 to 33 cm. when grown in fall under natural daylength with no growth regulators, and 20 to 25 cm. when grown in 10 cm. pots in spring with 1 to 2 applications of 2500 ppm B-9 SP.

*Branching pattern.*—Spreading and prolific, with 6 to 9 breaks after pinch when grown outside under natural daylength in fall flowerings, and 3 to 6 breaks after pinch when grown in 10 cm. pots for spring flowerings.

B. Foliage:

*Color (upper surface).*—147A.

*Color (under surface).*—147B.

*Shape.*—Small, lobed.

I claim:

1. A new and distinct Chrysanthemum plant named Cream Frolic, as described and illustrated.

* * * * *

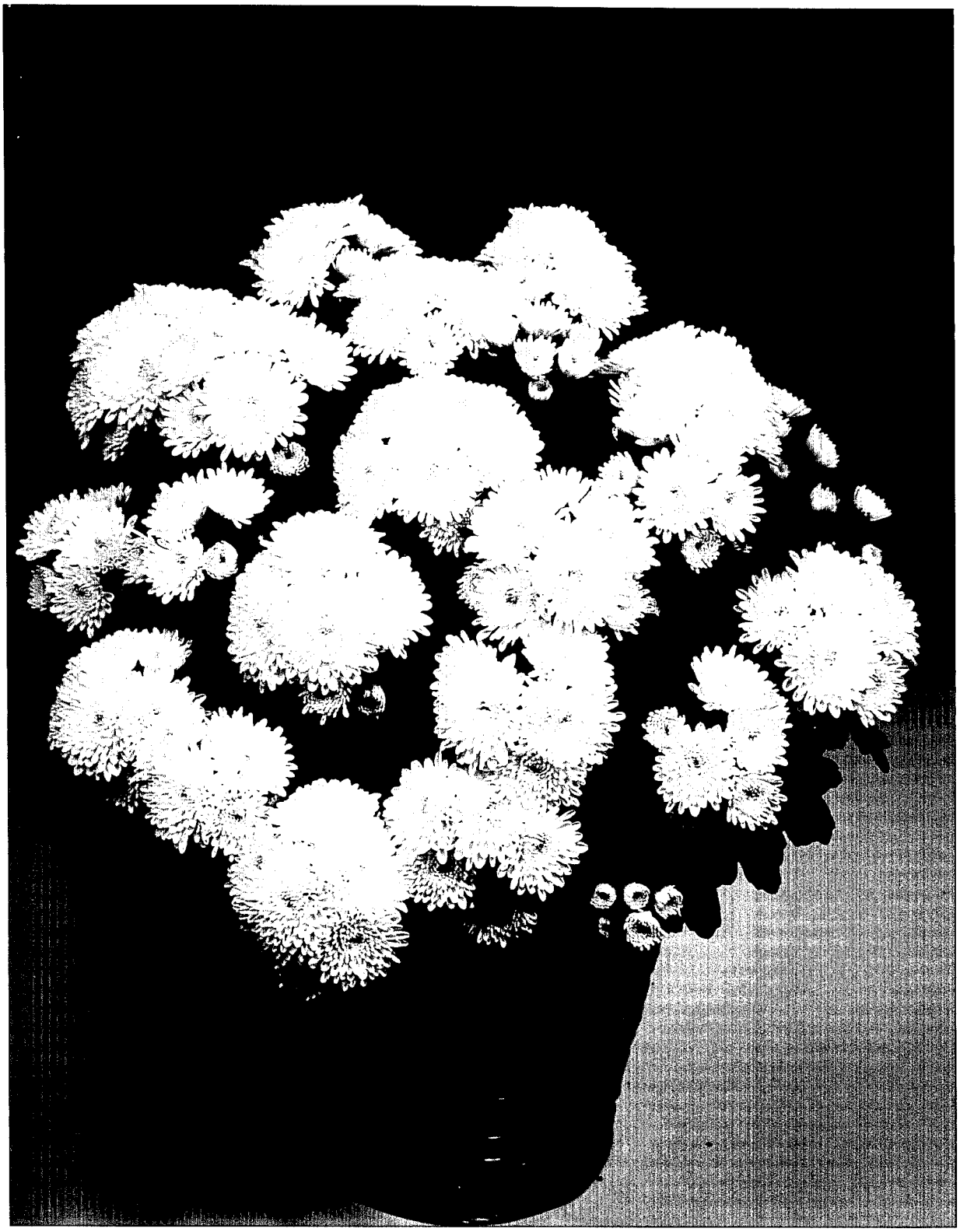

UNITED STATES PATENT AND TRADEMARK OFFICE

CERTIFICATE OF CORRECTION

PATENT NO. : PP 7,790

DATED : February 11, 1992

INVENTOR(S) : Cornelis P. VandenBerg

It is certified that error appears in the above-identified patent and that said Letters Patent is hereby corrected as shown below:

Column 1, line 24, "June 20" should read --July 20--.

Column 3, line 15, "trails" should read --trials--.

Signed and Sealed this

Twenty-third Day of November, 1993

*Attest:*

Bruce Lehman

BRUCE LEHMAN

*Attesting Officer*

*Commissioner of Patents and Trademarks*